United States Patent
Blomquist et al.

(10) Patent No.: US 11,967,292 B2
(45) Date of Patent: *Apr. 23, 2024

(54) DISPLAY FOR PUMP

(71) Applicant: Tandem Diabetes Care, Inc., San Diego, CA (US)

(72) Inventors: Michael L. Blomquist, Blaine, MN (US); Timothy B. Bresina, Shoreview, MN (US); Gail Beth Bynum, Brooklyn Park, MN (US); Michael D. Welsch, Stillwater, MN (US)

(73) Assignee: Tandem Diabetes Care, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/976,292

(22) Filed: Oct. 28, 2022

(65) Prior Publication Data

US 2023/0050496 A1 Feb. 16, 2023

Related U.S. Application Data (60) Continuation of application No. 17/034,264, filed on Sep. 28, 2020, now Pat. No. 11,488,549, which is a continuation of application No. 16/401,684, filed on May 2, 2019, now Pat. No. 11,580,918, which is a continuation of application No. 15/407,955, filed on Jan. 17, 2017, now Pat. No. 10,726,100, which is a continuation of application No. 13/242,116, filed on Sep. 23, 2011, now abandoned, which is a division of application No. 12/114,033, filed on May 2, 2008, now Pat. No. 8,133,197.

(51) Int. Cl.
| | |
|---|---|
| G09G 3/20 | (2006.01) |
| A61M 5/142 | (2006.01) |
| G09G 3/34 | (2006.01) |
| G16H 20/17 | (2018.01) |
| G16H 40/63 | (2018.01) |
| G16H 50/30 | (2018.01) |

(52) U.S. Cl.
CPC ............. G09G 3/344 (2013.01); A61M 5/142 (2013.01); G09G 3/2003 (2013.01); G09G 3/3466 (2013.01); G16H 20/17 (2018.01); G16H 40/63 (2018.01); G16H 50/30 (2018.01); A61M 2205/502 (2013.01); G09G 2330/022 (2013.01); G09G 2380/08 (2013.01)

(58) Field of Classification Search
CPC .. G09G 3/344; G09G 3/3466; G09G 2380/08; G09G 2330/022; G09G 3/2003; G06F 3/048; G16H 20/17; G16H 40/63; G16H 50/30; G06T 11/206
See application file for complete search history.

(56) References Cited

U.S. PATENT DOCUMENTS

| | | |
|---|---|---|
| 5,782,805 A | 7/1998 | Meinzer et al. |
| 5,822,715 A | 10/1998 | Worthington et al. |
| 7,033,338 B2 | 4/2006 | Vilks et al. |

(Continued)

*Primary Examiner* — Antonio A Caschera
(74) *Attorney, Agent, or Firm* — MERCHANT & GOULD P.C.

(57) ABSTRACT

An apparatus comprising a pump configured to deliver insulin, a processor, and a user interface including a color display. Color on the display can be used to bring a user's attention to a change in status of the device or a detected change in status of the patient.

17 Claims, 9 Drawing Sheets

(56) References Cited

U.S. PATENT DOCUMENTS

| | | |
|---|---|---|
| 7,042,643 B2 | 5/2006 | Miles |
| 9,238,100 B2 | 1/2016 | Kruse et al. |
| 9,335,910 B2 | 5/2016 | Farnan et al. |
| 9,381,296 B2 * | 7/2016 | Arrizza .................. A61M 5/142 |
| 9,486,171 B2 | 11/2016 | Saint |
| 9,669,160 B2 | 6/2017 | Harris et al. |
| 9,715,327 B2 | 7/2017 | Rosinko et al. |
| 9,814,835 B2 | 11/2017 | Kruse et al. |
| 9,833,177 B2 | 12/2017 | Blomquist |
| 9,867,937 B2 | 1/2018 | Saint et al. |
| 9,867,953 B2 | 1/2018 | Rosinko |
| 10,016,561 B2 | 7/2018 | Saint et al. |
| 10,052,049 B2 | 8/2018 | Blomquist et al. |
| 10,213,547 B2 | 2/2019 | Rosinko |
| 10,357,606 B2 | 7/2019 | Rosinko et al. |
| 10,357,607 B2 | 7/2019 | Blomquist et al. |
| 10,430,043 B2 | 10/2019 | Rosinko et al. |
| 10,434,253 B2 | 10/2019 | DiPerna et al. |
| 10,549,051 B2 | 2/2020 | Rosinko |
| 10,569,016 B2 | 2/2020 | Rosinko |
| 10,653,834 B2 | 5/2020 | Kruse et al. |
| 10,864,322 B2 | 12/2020 | Saint et al. |
| 10,943,687 B2 | 3/2021 | Blomquist |
| 10,994,077 B2 | 5/2021 | Rosinko |
| 11,116,901 B2 | 9/2021 | Harris |
| 11,135,362 B2 | 10/2021 | DiPerna et al. |
| D938,457 S | 12/2021 | Rosinko et al. |
| 11,224,693 B2 | 1/2022 | Ulrich et al. |
| 11,285,263 B2 | 3/2022 | DiPerna et al. |
| 11,291,763 B2 | 4/2022 | Blomquist et al. |
| 11,298,053 B2 | 4/2022 | Blomquist |
| 11,302,433 B2 | 4/2022 | Blomquist et al. |
| 11,324,898 B2 | 5/2022 | Rosinko |
| 11,464,908 B2 | 10/2022 | Michaud et al. |
| 11,488,549 B2 * | 11/2022 | Blomquist ........... G09G 3/3466 |
| 11,576,594 B2 | 2/2023 | Blomquist |
| 11,607,492 B2 | 3/2023 | Rosinko et al. |
| 11,638,781 B2 | 5/2023 | Rosinko |
| 11,676,694 B2 | 6/2023 | Kruse et al. |
| 11,694,794 B2 | 7/2023 | Farnan et al. |
| 2006/0229557 A1 | 10/2006 | Fathallah et al. |
| 2007/0093786 A1 * | 4/2007 | Goldsmith ......... A61B 5/14532 |
| | | 604/890.1 |
| 2008/0071580 A1 * | 3/2008 | Marcus .................. G16H 40/67 |
| | | 705/3 |
| 2008/0122796 A1 | 5/2008 | Jobs et al. |
| 2008/0206799 A1 | 8/2008 | Blomquist |
| 2008/0228056 A1 | 9/2008 | Blomquist et al. |
| 2008/0312512 A1 | 12/2008 | Brukalo et al. |
| 2009/0147026 A1 | 6/2009 | Buck et al. |
| 2009/0164239 A1 * | 6/2009 | Hayter .................. G16H 20/60 |
| | | 705/2 |
| 2010/0107150 A1 | 4/2010 | Kamada et al. |
| 2011/0152770 A1 | 6/2011 | DiPerna et al. |
| 2013/0283196 A1 | 10/2013 | Farnan et al. |
| 2013/0331778 A1 | 12/2013 | Kruse et al. |
| 2013/0332874 A1 | 12/2013 | Rosinko et al. |
| 2014/0171772 A1 | 6/2014 | Blomquist |
| 2014/0273042 A1 | 9/2014 | Saint |
| 2014/0276419 A1 | 9/2014 | Rosinko et al. |
| 2014/0276556 A1 | 9/2014 | Saint et al. |
| 2014/0350371 A1 | 11/2014 | Blomquist et al. |
| 2014/0378898 A1 | 12/2014 | Rosinko |
| 2015/0073337 A1 | 3/2015 | Saint et al. |
| 2015/0120317 A1 | 4/2015 | Mayou et al. |
| 2016/0030669 A1 | 2/2016 | Harris et al. |
| 2016/0082188 A1 | 3/2016 | Blomquist et al. |
| 2016/0121047 A1 | 5/2016 | Kruse et al. |
| 2016/0199571 A1 | 7/2016 | Rosinko et al. |
| 2016/0271325 A1 | 9/2016 | Farnan et al. |
| 2017/0000943 A1 | 1/2017 | Blomquist et al. |
| 2017/0043085 A1 | 2/2017 | Rosinko |
| 2017/0056590 A1 | 3/2017 | DiPerna et al. |
| 2017/0182248 A1 | 6/2017 | Rosinko |
| 2017/0300206 A1 | 10/2017 | Rosinko et al. |
| 2018/0064873 A1 | 3/2018 | Kruse et al. |
| 2018/0092578 A1 | 4/2018 | Blomquist |
| 2018/0110921 A1 | 4/2018 | Saint et al. |
| 2018/0193573 A1 | 7/2018 | Rosinko |
| 2018/0361060 A9 | 12/2018 | Rosinko |
| 2019/0321552 A1 | 10/2019 | DiPerna et al. |
| 2019/0328967 A1 | 10/2019 | Blomquist |
| 2019/0350501 A1 | 11/2019 | Blomquist et al. |
| 2019/0365997 A1 | 12/2019 | Harris |
| 2019/0388015 A1 | 12/2019 | Blomquist |
| 2020/0012401 A1 | 1/2020 | Rosinko et al. |
| 2020/0016335 A1 | 1/2020 | DiPerna et al. |
| 2020/0101226 A1 | 4/2020 | Rosinko et al. |
| 2020/0114076 A1 | 4/2020 | Ulrich et al. |
| 2020/0171249 A1 | 6/2020 | Rosinko |
| 2020/0179603 A1 | 6/2020 | Rosinko |
| 2020/0254174 A1 | 8/2020 | Kruse et al. |
| 2020/0261649 A1 | 8/2020 | Michaud et al. |
| 2020/0368430 A1 | 11/2020 | Ulrich et al. |
| 2021/0001044 A1 | 1/2021 | Michaud et al. |
| 2021/0012876 A1 | 1/2021 | Blomquist |

* cited by examiner

DISPLAY FOR PUMP

RELATED APPLICATIONS

This application is a continuation of application Ser. No. 17/034,264, filed Sep. 28, 2020, which in turn is a continuation of application Ser. No. 16/401,684, filed May 2, 2019, which in turn is a continuation of application Ser. No. 15/407,955, filed Jan. 17, 2017, now U.S. Pat. No. 10,726,100, issued Jul. 28, 2020, which in turn is a continuation of application Ser. No. 13/242,045, filed Sep. 23, 2011, now U.S. Pat. No. 9,378,333, issued Jun. 28, 2016, which in turn is a continuation of application Ser. No. 13/242,116, filed Sep. 23, 2011, now abandoned, which in turn is a division of application Ser. No. 12/114,033, filed May 2, 2008, now U.S. Pat. No. 8,133,197, issued Mar. 13, 2012, each of which are hereby fully incorporated herein by reference.

BACKGROUND

People who suffer from diabetes require insulin to keep their blood glucose level as close as possible to normal levels. It is essential for people with diabetes to manage their blood glucose level to within a normal range. Complications from diabetes can include heart disease (cardiovascular disease), blindness (retinopathy), nerve damage (neuropathy), and kidney damage (nephropathy). Insulin is a hormone that reduces the level of blood glucose in the body. Normally, insulin is produced by beta cells in the pancreas. In non-diabetic people, the beta cells release insulin to satisfy two types of insulin needs. The first type is a low-level of background insulin that is released throughout the day. The second type is a quick release of a higher-level of insulin in response to eating. Insulin therapy replaces or supplements insulin produced by the pancreas.

Conventional insulin therapy typically involves one or two injections a day. The low number of injections has the disadvantage of allowing larger variations in a person's insulin levels. Some people with diabetes manage their blood glucose level with multiple daily injections (MDI). MDI may involve more than three injections a day and four or more blood glucose tests a day. MDI offers better control than conventional therapy. However, insulin injections are inconvenient and require a diabetic person to track the insulin doses, the amount of carbohydrates eaten, and their blood glucose levels among other information critical to control.

It is important for a diabetic person to be treated with the proper amount of insulin. As discussed previously, high blood sugar can lead to serious complications. Conversely, a person with low blood sugar can develop hypoglycemia. Ideally, insulin therapy mimics the way the body works. An insulin pump is one way to mimic the body's insulin production. An insulin pump can provide a background or basal infusion of insulin throughout the day and provide a quick release or bolus of insulin when carbohydrates are eaten. If a person develops high blood sugar, a correction bolus can be delivered by the pump to correct it. While insulin pumps improve convenience and flexibility for a diabetic person, they can be sophisticated devices. Some insulin pumps can be difficult to program. It is desirable for an insulin pump to have features that make the pump more convenient or more effective for the patient to use.

Overview

This document discusses, among other things, devices and methods for assisting a diabetic person manage insulin therapy. A device example includes a pump configured to deliver insulin, a processor, and a user interface that includes a bistable display. A display element of the bistable display is placed in one of two stable orientations upon application of a biasing voltage. The display element stays in the stable orientation when the biasing voltage is removed. The processor includes a display module configured to display a non-blank reversion display screen on the bistable display when no input is received at the user interface after a specified time duration, and to recurrently change the reversion display screen until input is received at the user interface.

A method example includes providing a bistable display on a device having an insulin pump, reverting the display to a non-blank reversion display screen when no input is received at a user interface after a specified time duration, and recurrently changing the reversion display screen until input is received at the user interface.

This section is intended to provide an overview of subject matter of the present patent application. It is not intended to provide an exclusive or exhaustive explanation of the invention. The detailed description is included to provide further information about the subject matter of the present patent application.

DETAILED DESCRIPTION

Figure 1A:
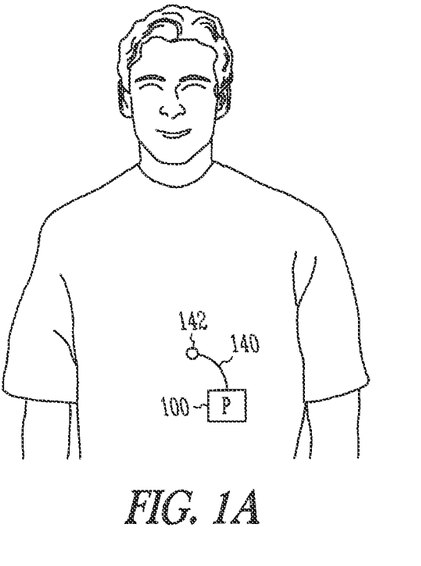
FIGS. 1A and 1B illustrate portions of a device that includes an insulin pump.
Figure 1B:
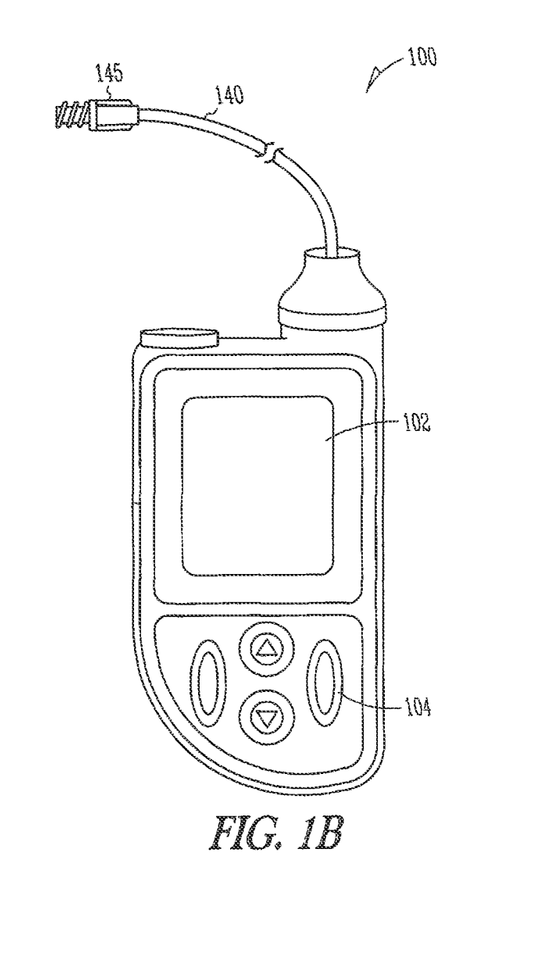

Insulin pump features may assist an insulin pump user in being more effective in treating their diabetes. FIGS. 1A and 1B illustrate portions of a device 100 that includes an insulin pump. The device 100 includes a cassette or cartridge of insulin. The cartridge is connectable to infusion tubing 140 connectable to a patient such as by a Luer lock 145 or infusion set 142. The device 100 includes a display 102 and a user interface that may include the display 102 and include one or more keys 104. Because proper use of an insulin pump often requires a user to go through a learning curve to properly treat their diabetes using the pump, it is desirable for a pump to provide assistance to the user in operating the pump, whether the user is a diabetic patient, a caregiver, or a clinician. Device displays are a useful way to provide information to the user.

Bistable Display

Ambulatory insulin pumps are typically battery powered. It is desirable to reduce power consumption in an ambulatory insulin pump device to extend the lifetime of the battery power source. Displays for the insulin pump devices typically require power to maintain the display. For example, organic light emitting diodes (OLEDs) require constant power source to generate light. Liquid crystal displays (LCDs) typically require a refresh cycle to periodically update the display. LCDs may also require backlighting to illuminate pixels of the display. These examples require power to maintain the display even if the information on the display does not change.

In a bistable display, a display element (e.g., a pixel or a subpixel) is placed in one of two stable orientations upon application of a biasing voltage, and the display element stays in the stable orientation when the biasing voltage is removed. Thus, a bistable display mainly requires power only when changing the orientation of the display element, and requires little or no power to maintain the orientation.

An example of a bistable display is an electrophoretic display (EPD). In an EPD, particles in the display acquire charge from the biasing voltage. The polarity of the voltage determines whether the charged particle will have a black appearance (the first stable orientation) or white appearance (the second stable orientation). Ambient reflected light is used to read the display similar to the way ambient light is used to read a newspaper. EPDs are sometime referred to as electronic paper (e-paper) or electronic ink (e-ink).

Another example of a bistable display is an interferometric modulator (IMOD) display. In some embodiments of an interferometric modulator display, application of a voltage causes a display element to have black appearance (the first stable orientation), and application of a lower voltage causes the display to appear bright and colored (the second stable state). In a bichrome display, the display element is a pixel and the bias voltage is applied to a pixel. In a color display, a color pixel is comprised of a grid of display elements called sub-pixels and the bias voltage is applied to a sub-pixel. The sub-pixels exhibit different colors when the lower voltage is applied and produce the same color (e.g., black) when the bias voltage is applied. Together, the sub-pixels provide a full color display using spatial dithering. A description of IMOD displays is found in U.S. Pat. No. 7,042,643, "Interferometric Modulation of Radiation," filed Feb. 19, 2002, which is incorporated herein in its entirety.

Because a bistable display requires little or no power to maintain the display, the display will likely appear the same whether the insulin pump is working or the insulin pump has malfunctioned. This may make it difficult for an insulin pump user to notice when the device has malfunctioned.

Figure 2:
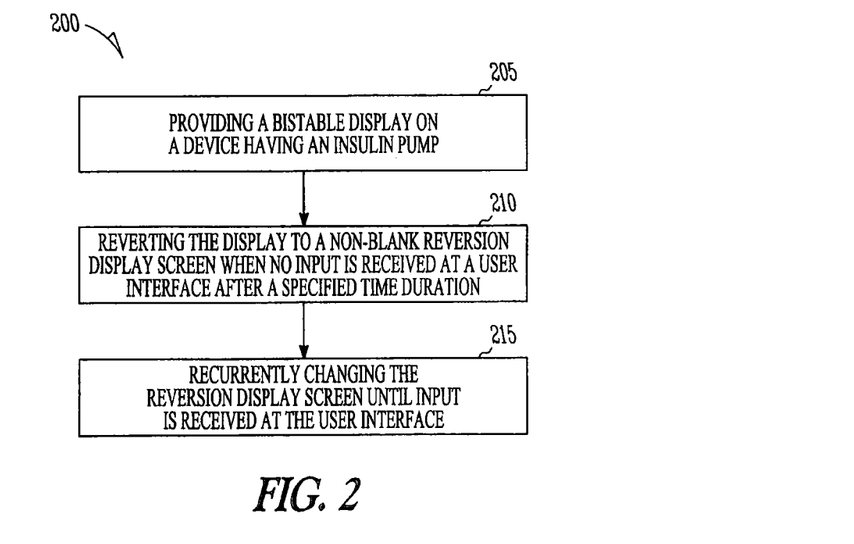
FIG. 2 is a flow diagram of a method of presenting an insulin pump display to a user.

FIG. 2 is a flow diagram of a method 200 of presenting an insulin pump display to a user. At block 205, a bistable display is provided on a device having an insulin pump. The display is bistable because a display element (e.g., a pixel or sub-pixel) may be placed in one of two stable orientations upon application of a biasing voltage, and the display element stays in the stable orientation when the biasing voltage is removed.

At block 210, the bistable display reverts to a non-blank reversion display screen when no input is received at a user interface of the insulin pump device after a specified time duration. For example, the reversion screen may be an icon from the manufacturer or a photo the user downloads into the insulin pump device. However, because of the nature of a bistable display, a user would not be able to notice from a simple reversion screen whether the device is still functioning properly.

At block 215, the reversion display screen is recurrently changed until input is received at the user interface. In some embodiments, recurrently changing the reversion display screen may include recurrently changing from one of a plurality of reversion display screens to another of the plurality of display screens. In some embodiments, recurrently changing the reversion display screen may include recurrently producing an animated effect on a single reversion display screen. In some embodiments, recurrently changing the reversion display screen may include switching among several display screens to create an animated effect, such as sequentially displaying animation frames to produce an animated effect. Use of reversion screens may assist a user in operating their insulin pump device.

Figure 3:
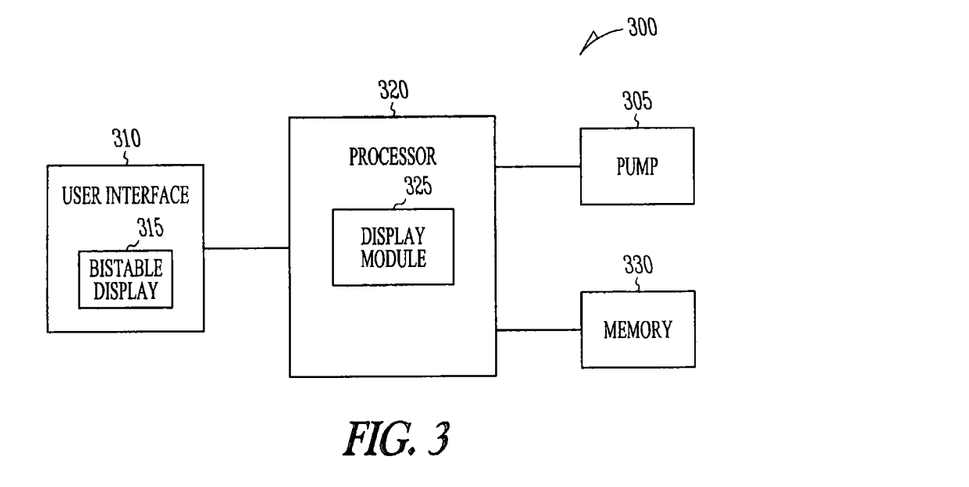
FIG. 3 is a block diagram of portions of an embodiment of an insulin pump device.

FIG. 3 is a block diagram of portions of an embodiment of an insulin pump device 300. The insulin pump device 300 includes a pump 305 configured to deliver insulin and a user interface 310. The pump 305 may be a positive displacement pump. Descriptions of an example of a medication pump to deliver insulin are found in Vilks et al., "Cartridge and Rod for Axially Loading a Medication Pump," U.S. Pat. No. 7,033,338, filed Feb. 28, 2002, which is incorporated herein by reference in its entirety. The pump 305 may drive a plunger in a removable insulin cartridge to deliver the insulin.

The user interface 310 includes a bistable display 315. In some embodiments, the bistable display 315 includes an interferometric modulation display. In some embodiments, the bistable display 315 includes an electrophoretic display. In some embodiments, the bistable display 315 includes an EPD. The substrate for the EPD may be made of flexible plastic. This provides a robust and thin display for the insulin pump device 300.

The insulin pump device 300 also includes a processor 320. The processor 320 may be a microprocessor, digital signal processor (DSP), or other type of processor. The processor 320 is configured to perform or execute a function or functions. Such functions correspond to modules to provide features integral to the first device. Modules may be software, hardware, firmware or any combination thereof. Multiple functions may be performed in one or more modules. In some embodiments, software or firmware is provided on a computer readable medium. The computer readable medium includes instructions therein, which when processed (such as by the processor 320 for example) results in a device performing the functions described herein. Examples of a computer readable medium include a compact disc (CD), memory stick, or remote storage accessible via a communication network such as the internet or a cell phone network.

The processor 320 is communicatively coupled to the pump 305 and the user interface 310. The communicative coupling allows the processor 320 to exchange electrical signals with the pump 305 and the user interface 310 even though intervening circuitry may be present. The processor 320 includes a display module 325 configured to display a non-blank reversion display screen on the bistable display 315 when no input is received at the user interface 310 after a specified time duration, and to recurrently change the reversion display screen until input is received at the user interface.

In some embodiments, the display module 325 is configured to produce an animated effect on the reversion display screen. For example, the animated effect may be a moving icon. The display module 325 recurrently produces the animated effect on the reversion display screen until input is received at the user interface 310. At which point the display module 325 may change from the reversion screen display to a home menu display.

In an illustrative example, the moving icon may be a clock and the animated effect may be moving hands of the clock. The display module 325 periodically produces the animated effect by moving the hands of the clock to display time according to a timer of the processor. In some embodiments, the display module 325 is configured to display time on the reversion display screen by displaying numbers on the display screen and updating the numbers according to the time.

According to some embodiments, the insulin pump device 300 includes a memory 330 communicatively coupled to the processor 320. The memory 330 stores a plurality of reversion display screens, and the display module 325 is configured to display one of the plurality of reversion display screens when no input is received at the user interface after a specified time duration, and to recurrently change the reversion display screen from one of the plurality of reversion display screens to another of the plurality of reversion display screens while no input is received at the user interface 310. The reversion display screen would change after a time duration, such as every few seconds for example.

In some embodiments, the display module 325 is configured to change the reversion display screen in response to input received via the user interface. For example, as a test to verify the insulin pump device 300 is working properly, the reversion display screen would change when the user presses a specified user interface key or button. In another example, the user may use the user interface 310 to advance through several reversion display screen options and indicate a desired display screen. In certain embodiments, the memory 330 stores an indication that a reversion display screen is selected by a user. The display module 325 only displays one or more reversion screens selected by the user. In certain embodiments, one or more reversion screens are images downloaded by the user, such as photos for example. The display module 325 may display the images in a slide-show fashion.

Various events may cause the display module 325 to change the bistable display 315 from a reversion screen. In some embodiments, the display module 325 changes the bistable display 315 from the reversion display screen to a home menu when input is received at the user interface 310. In some embodiments, the display module 325 changes the bistable display 315 from the reversion display screen in response to a change in status of the insulin pump device 300. For example, the change in status may be related to a problem of the insulin pump device 300, such as an insulin cartridge containing less than a threshold level of insulin, a device battery having a capacity less than a threshold battery capacity value, or an indication that the insulin pump device is not operating correctly. The display module 325 may change to an alarm display screen to indicate a problem to the user, may change to a debug display screen to help the user determine the problem, or may display both an alarm display screen and a debug display screen.

In some embodiments, the display module 325 changes the reversion display screen in response to a detected change in a clinical status of a user. The change in clinical status may include at least one of a recent blood glucose reading being higher than a first threshold blood glucose value, a recent blood glucose reading being lower than the same threshold blood glucose value or a second threshold blood glucose value, the user exercising within a specified time period, the user eating within a specified time period, the user not eating within a specified time period, or the user having active insulin in their body. The display module 325 may change to an alarm display screen to indicate the change in clinical status to the user.

Custom Display Menus

Insulin pumps may be able to provide a variety of therapies and diagnostics for the user. Accessing the functions of the device may include navigating through several layers of device menus. It would be helpful to the user if the display menus are customized for the user. The menus may be automatically customized according to which functions are used most often, according to which functions are more appropriate for the users clinical status, or the menus may be manually customized by the user directly.

Figure 4:
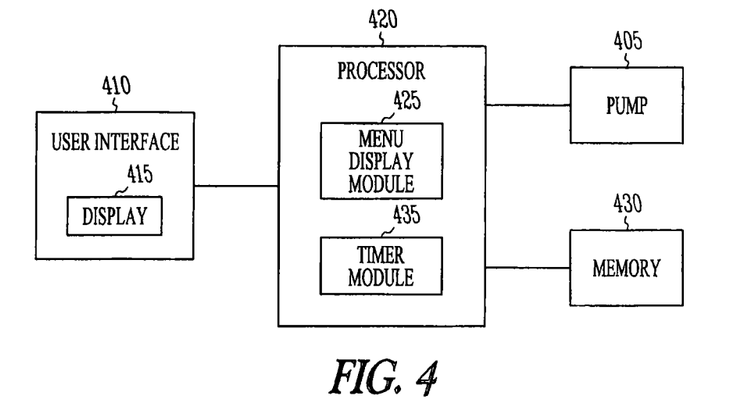
FIG. 4 is a block diagram of portions of another embodiment of an insulin pump device.

FIG. 4 is a block diagram of portions of an embodiment of an insulin pump device 400. The insulin pump device 400 includes a pump 405 configured to deliver insulin and a user interface 410 that includes a display 415. In some embodiments, the display 415 is a bistable display. The insulin pump device 400 also includes a processor 420 communicatively coupled to the pump 405 and the user interface 410. The processor 420 includes a menu display module 425. The menu display module 425 presents one of a plurality of device menus on the display 415.

Figure 5:
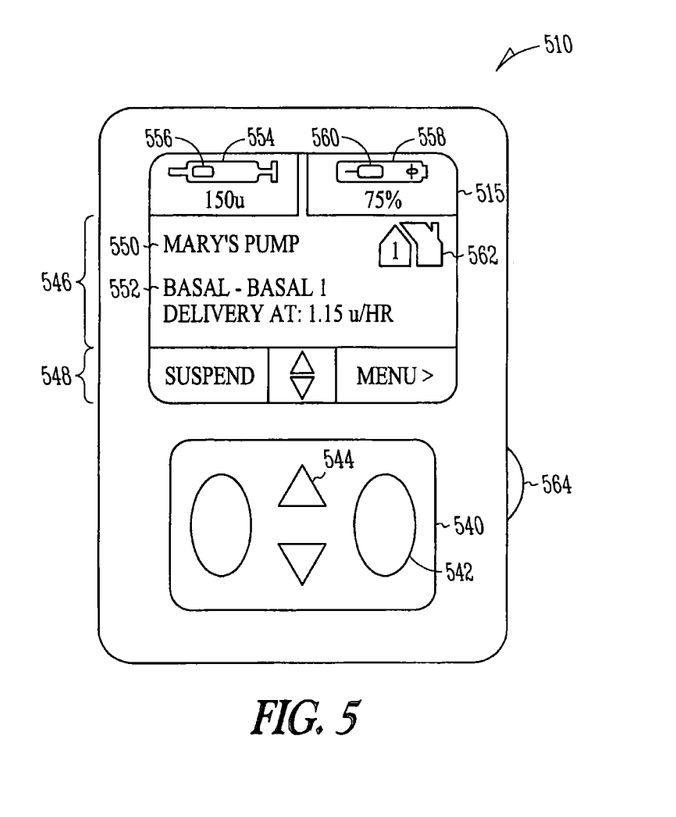
FIG. 5 shows an illustration of an example user interface with a display screen.

FIG. 5 shows an illustration of an example user interface 510 with a display screen 515. The user interface 510 includes a keypad 540 including function keys 542 and scroll keys 544 or up/down keys. The display screen 515 shows an example display menu having menu items. The user interface 510 receives a selection of a menu item included in a display menu. Selecting a menu item causes the processor to perform an action, such as indicating a status of the insulin pump device, modifying an operation parameter, or initiating a device task.

The example display menu shown has a top portion 546 and a bottom portion 548. The top portion 546 may show a display banner 550 identifying the pump as "Mary's Pump". The display banner 550 may be customized by the user via the keypad 540. The example display menu is one shown during active delivery of basil insulin. The display menu indicates basal insulin is being delivered at a rate of 1.15 units/hour according to a first basal schedule. The top portion 546 may present the name 552 of the active function and details of the function performed.

The bottom portion indicates the current function of the keys 542, 544. In the display shown, the pressing the left function key suspends the basal delivery. If delivery is suspended, the function of the left function key may change to activating the delivery. The right function key advances the display screen to a different display menu. The up/down keys retain the up/down function. For example, the scroll keys 544 may be used to highlight the name 552 of the active function in order to change from the first basal schedule.

The example display menu also shows a first icon 554 and a bar 556 to show the amount of insulin remaining in the insulin cartridge, and a second icon 558 and a bar 560 to indicate the remaining battery life. The example display menu also shows a third icon 562 to identify the display menu as the home menu or home page for the user.

Returning to FIG. 4, it was noted that the menu display module 425 presents one of a plurality of device menus on the display 415. The menu display module 425 arranges the device menus into an order for presentation according to user preference information. In some embodiments, the user preference information includes the frequency that certain menus are used. The menu display module 425 tracks device menu selections made via the user interface 410. The menu display module 425 then arranges the device menus into a presentation order according to a frequency with which device menus are used. For example, if the user frequently accesses the basal delivery display menu, the menu display module 425 moves the basal delivery display menu closer to the beginning of the order with which device menus are displayed.

According to some embodiments, the user preference information includes information regarding the clinical status of the user. The information may be entered into a memory 430 of the device via the user interface 410 or may be downloaded into the memory 430 via a communication port. The processor 420 receives the clinical status information and the menu display module 425 arranges the device menus into the presentation order according to the clinical status information.

For example, the clinical status information may indicate that the user has delayed gastric emptying. A user with delayed gastric emptying may use an extended or combination bolus of insulin. Descriptions of insulin pump devices that provide extended and combination boluses are found in Blomquist, U.S. patent application Ser. No. 11/679,712, "Carbohydrate Ratio Test Using Frequent Blood Glucose Input," filed Feb. 27, 2007, which is incorporated herein by reference in its entirety. The menu display module 425 may make it more convenient for the user to access the display menu used to program and initiate an extended and/or combination bolus (e.g., the extended bolus menu may be presented before the standard bolus display menu).

In another example, the clinical status information may include an indication that the user has a high or low blood glucose reading. The menu display module 425 may make it more convenient (e.g., displayed sooner in a hierarchy) for the user to access a display menu that is used when measuring blood glucose. The menu display module 425 may also make it more convenient for the user to access the blood glucose measurement display menu if the user is performing basal rate testing. Descriptions of devices that automatically perform basal rate testing are found in Blomquist, U.S. patent application Ser. No. 11/685,617, "Basal Rate Test Using Frequent Blood Glucose Input," filed Mar. 13, 2007, which is incorporated herein by reference in its entirety.

According to some embodiments, the processor 420 determines information regarding eating times of the user. The processor 420 may determine the information by receiving the information through a communication port or via a user interface. The processor 420 may determine the information by deducing the information regarding eating times from other programmed parameters, such as programmed meal boluses or programmed missed meal bolus alarms. In some embodiments the processor 420 may determine the information by learning the eating times of the user, such as by tracking the times a meal bolus is initiated for example.

The menu display module 425 arranges the device menus into the presentation order according to the eating times of the user. For example, based on the information, the menu display module 425 may arrange the display menus in anticipation of the user initiating a post-prandial blood glucose test, and make the blood glucose measurement display menu more convenient for the user to access.

According to some embodiments, the processor 420 includes a timing module 435. The menu display module 425 arranges the device menus into the presentation order according to a time of day. For example, the menu display module 425 may make it more convenient for the user to access a display menu used to program and/or initiate a meal or correction bolus based on time the user typically exercises or eats. In another example, if the user checks their blood glucose at a specific time of day, the menu display module 425 may make the blood glucose measurement display menu more convenient for the user to access at those times. In still another example, the user may disconnect the pump or change the insulin cartridge at specific times of day. The menu display module 425 may make the related display menus easier for the user to access at those times.

In some embodiments, the user enters the user preference information via the user interface. For example, the user enters an indication of which display menu she wishes to display as the home display menu. The processor 420 receives the user preference information and the menu display module 425 arranges the device menus into the presentation order according to the received user preference information.

The menu items included in a home menu are a subset of all available menu items. In some embodiments, the menu display module includes menu items in the home menu according to the user preference information. For example, the user may provide, via the user interface 410, an indication that the battery icon of FIG. 5 should be placed in the home menu. In certain embodiments, the processor 420 includes the timing module 435 and the user preference information includes a display reversion time duration. The menu display module 425 reverts from a displayed menu to the home menu when no displayed menu items are selected during the display reversion time duration.

In some embodiments, the menu display module 425 tracks device menu selections made via the user interface. The menu display module 425 includes menu items in the device home menu according to a frequency with which menu items are used. For example, if the user frequently checks how much insulin is remaining in the insulin cartridge, the menu display module 425 adds the insulin remaining icon to the home menu.

According to some embodiments, the insulin pump device 400 includes a memory 430 communicatively coupled to the processor to store a database of food options in association with a known amount of nutrient content. Nutrient content includes one or more of the amount of carbohydrates, fat, protein, or fiber in an amount of a type of food. The menu display module 425 displays food options in one or more display menus. The user indicates the food she is going to eat and the processor 420 may use the nutrient content for the indicated food option to determine an amount of insulin in a meal bolus or to determine a type of meal bolus for the user.

In some embodiments, the menu display module 425 is configured to track selections from the food database made by the user. The menu display module 425 may than arrange a viewing order of entries in the food database according to a frequency with which entries are selected. For example, if the user often selects pizza for lunch, the menu display module 425 may select that food option first when the food database menu is accessed at lunchtime.

In some embodiments, the user interface 410 includes a programmable tactile switch or button (e.g., tactile switch 564 in FIG. 5). The processor 420 is configured to initiate an action upon activation of the tactile switch. The processor action is specified in the user preference information. Thus, the tactile switch may be a generic switch or button until it is programmed by the user. For example, the tactile switch may be programmed to initiate a type of insulin bolus, to bring a specific display menu, or to activate a type of alarm provided by the insulin pump device 400.

Figure 6:
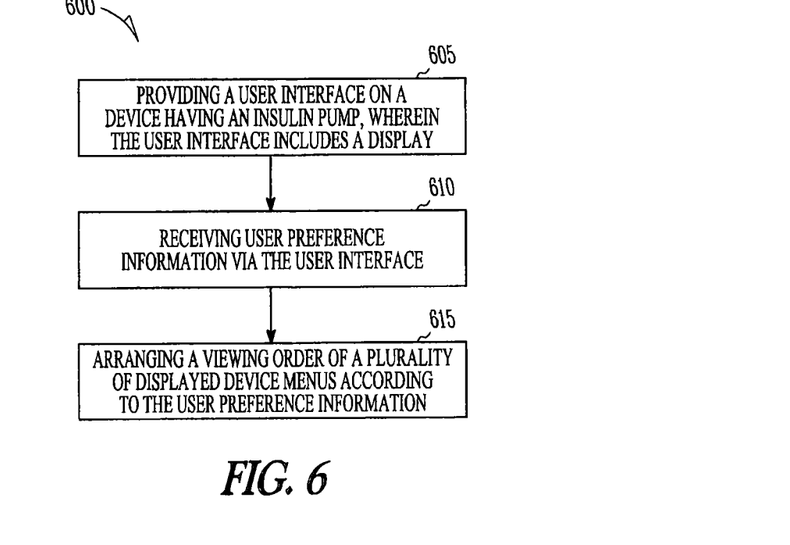
FIG. 6 is a flow diagram of another method of presenting an insulin pump display to a user.

FIG. 6 is a flow diagram of a method 600 of presenting an insulin pump display to a user. At block 605, a user interface is provided on a device having an insulin pump. The user interface includes a display. At block 610, user preference information is received into the device via the user interface. At block 615, a viewing order of a plurality of displayed device menus is arranged according to the user preference information.

Color Display

Information presented on a display is not of much use to the user if the user does not notice the information. Color on a display can be used to bring a user's attention to a change in status of the device or a detected change in status of the patient.

Figure 7:
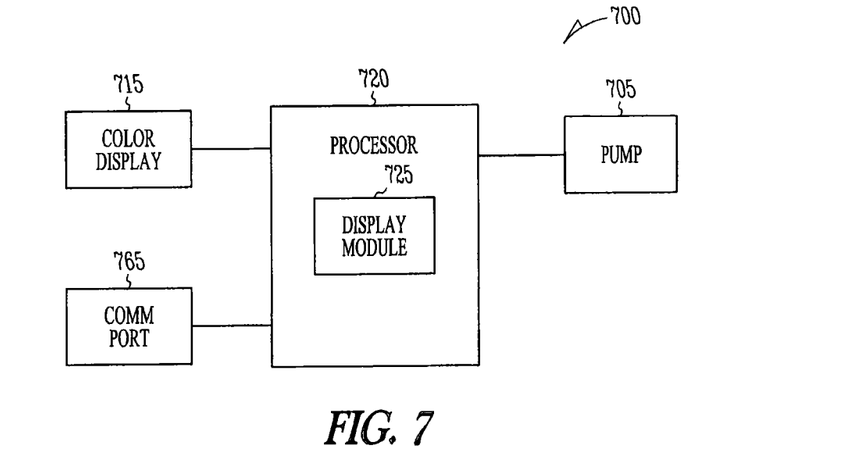
FIG. 7 is a block diagram of portions of an embodiment of an insulin pump device.

FIG. 7 is a block diagram of portions of an embodiment of an insulin pump device 700. The insulin pump device 700 includes a pump 705 configured to deliver insulin and a color display 715. In some embodiments, the color display 715 includes a color bistable display. The insulin pump device 700 also includes a processor 720 that comprises a display module 725 to display information related to clinical status of a user using a color indication and to change the color indication in response to a change in clinical status of the user.

Examples of a change in clinical status of the user include, among other things, a recent blood glucose reading being higher than a first threshold blood glucose value, a recent blood glucose reading being lower than the same threshold blood glucose value or a second threshold blood glucose value, the user exercising within a specified time period, the user eating within a specified time period, the user not eating within a specified time period, and the user having active insulin in their body.

Examples of change in a color indication used in the display 715 include, among other things, a change in a display background color, a change in a display backlight color, a change in a text color, and a color flashing indicator. The display module 725 changes the color indication when the clinical status changes. For example, the display module 725 may use a first display color when the user selects an insulin bolus display menu and there is no active insulin in the user's body, and uses a second display color when the user selects an insulin bolus display menu and there is active insulin in the user's body. In another example, the display module 725 may flash the insulin bolus display menu with the first or second display color when there is active insulin in the user's body.

In another embodiment, the change in a color indication is a gradual change. For example, the display module 725 may gradually change the color indication according to an amount of insulin that is active in the user, such as by gradually fading from the second display color to the first display color as the amount of active insulin decreases.

According to some embodiments, the display module 725 generates a device report on the color display 715. The processor 720 stores events in a memory integral to or communicatively coupled to the processor 720. The events may include historical insulin delivery information, recorded use parameters, and changes in the clinical status of the user. The display module 725 displays the device report and uses a color indication to show a change in clinical status.

In some embodiments, the insulin pump device includes a communication port 765 communicatively coupled to the processor 720. In some embodiments, the communication port 765 is a wireless port, such as an infrared (IR) port or a radio frequency (RF) port for example. In some embodiments, the communication port 765 is a wired port, such as a serial port for example. The processor 720 communicates the generated device report to a second separate device via the communication port, such as for printing of the device report or for displaying the device report for example.

Figure 8:
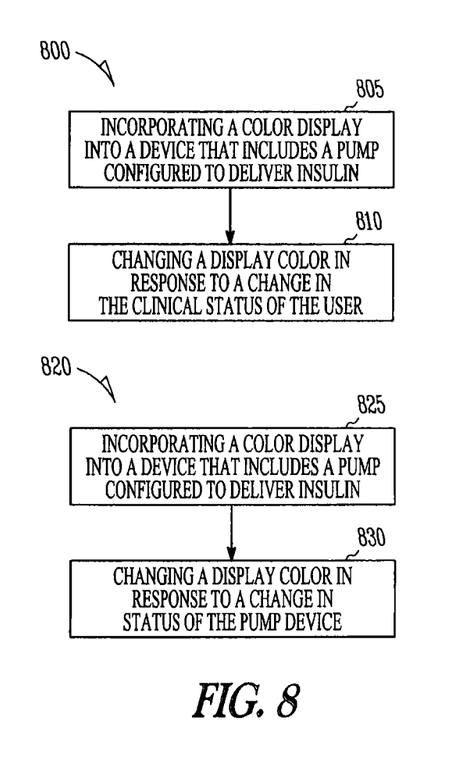
FIG. 8 shows a flow diagram of another method of presenting an insulin pump display to a user.

FIG. 8 shows a flow diagram of a method 800 of presenting an insulin pump display to a user. At block 805, a color display is incorporated into a device that includes a pump configured to deliver insulin. At block 810, a display color is changed in response to a change in clinical status of the user.

Returning to FIG. 7, according to some embodiments, the display module 725 is configured to change the color indication in response to a change in status of the insulin pump device. Examples of a change in status of the insulin pump device include, among other things, an insulin cartridge containing less than a threshold level of insulin, a device battery having a capacity less than a threshold battery capacity value, or an indication that the insulin pump device (e.g., the pump 705 itself) has stopped operating.

FIG. 8 also shows a flow diagram of a second method 820 of providing an insulin pump display to a user. At block 825, a color display is incorporated into a device that includes a pump configured to deliver insulin. In some embodiments, a color bistable display is incorporated into the device. At block 830, a display color is changed in response to a change in status of the insulin pump device.

Alternative Remote Display

Insulin pumps continue to decrease in size as technology advances. However, bigger displays are sometimes desirable for training on the devices or if the user has impaired vision.

Figure 9:
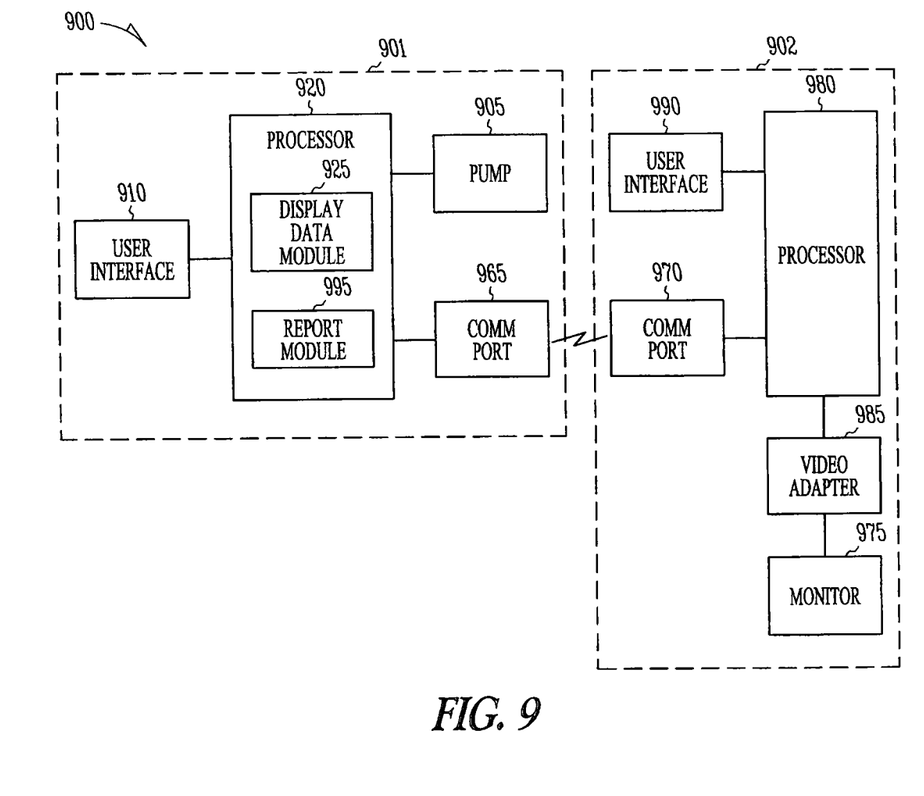
FIG. 9 is a block diagram of portions of an embodiment of system for providing a display for an insulin pump device.

FIG. 9 is a block diagram of portions of an embodiment of system 900 for providing a display for an insulin pump device. The system 900 comprises an insulin pump device 901 and a display device 902. The insulin pump device 901 includes a pump 905 configured to deliver insulin, a user interface 910, a communication port 965, and a first processor 920 communicatively coupled to the pump 905, the user interface 910, and the communication port 965.

The display device 902 includes a communication port 970, a monitor 975, and a second processor 980 communicatively coupled to the communication port 970 and the monitor 975. The first processor 920 includes a display data module 925 that communicates display information from the insulin pump device to the display device 902 via the communication ports 965, 970.

In some embodiments, the communication ports 965, 970 are wireless ports, such as an IR ports or RF ports for example. The insulin pump device 901 and the display device may communicate using a wireless protocol such as Bluetooth protocol, the WiFi protocol, or the infrared data (IrDA) protocol. In some embodiments, the communication ports 965 are wired ports, such as serial ports for example. The insulin pump device 901 and the display device may communicate using the universal serial bus (USB) protocol.

Input signals received at the user interface 910 change operation of the insulin pump device 901. These changes are reflected on the monitor 975 of the display device 902. The data display module 925 converts input received via the user interface 910 into changes to a display, and communicates updated display information according to the received input to the display device 902. The second processor receives the display information via the communication port 970 and displays a user menu for the insulin pump device 901 on the monitor 975.

Examples of display information communicated by the display data module 925 to the display device 902 include, among other things, an indication of status of the insulin pump device, a prompt to initiate a task by the insulin pump device, or an operation parameter of the insulin pump device. In some embodiments, the display data module 925 communicates, for display on the display device 902, instructions for using the insulin pump device 901. This is useful for training a new user to operate the insulin pump device 901.

The monitor 975 may be a larger display than is available for the insulin pump device 901, and the second processor 980 may display an enlarged version of the user menu for the insulin pump device 901 on the monitor 975. This allows the user to easily see how the input into the user interface 910 has effected operation of the insulin pump device 901. In some embodiments, the monitor 975 is a video monitor and the display device 902 includes a video adapter 985 communicatively coupled to the second processor 980 and the video monitor to convert the received display information to a video format for display on the video monitor.

According to some embodiments, the display device 902 includes a second user interface 990 communicatively coupled to the second processor 980. The second processor 980 manipulates the user menu for the insulin pump device 901 on the monitor 975 according to input received via the second user interface 990. Thus, the user menu displayed on the display device 902 may be changed according to input received via the second user interface 990. For example, the second user interface 990 allows the second processor to change a contrast of the user menu for the insulin pump device displayed on the monitor, a size of the user menu for the insulin pump device displayed on the monitor, or a color used in the displaying the user menu for the insulin pump device on the monitor.

According to some embodiments, the first processor 920 includes a report module 995 to generate a device report. As described previously, the device report may include historical insulin delivery information, recorded use parameters, and changes in the clinical status of the user. The display data module 925 communicates the device report to the display device 902 for display.

Figure 10:
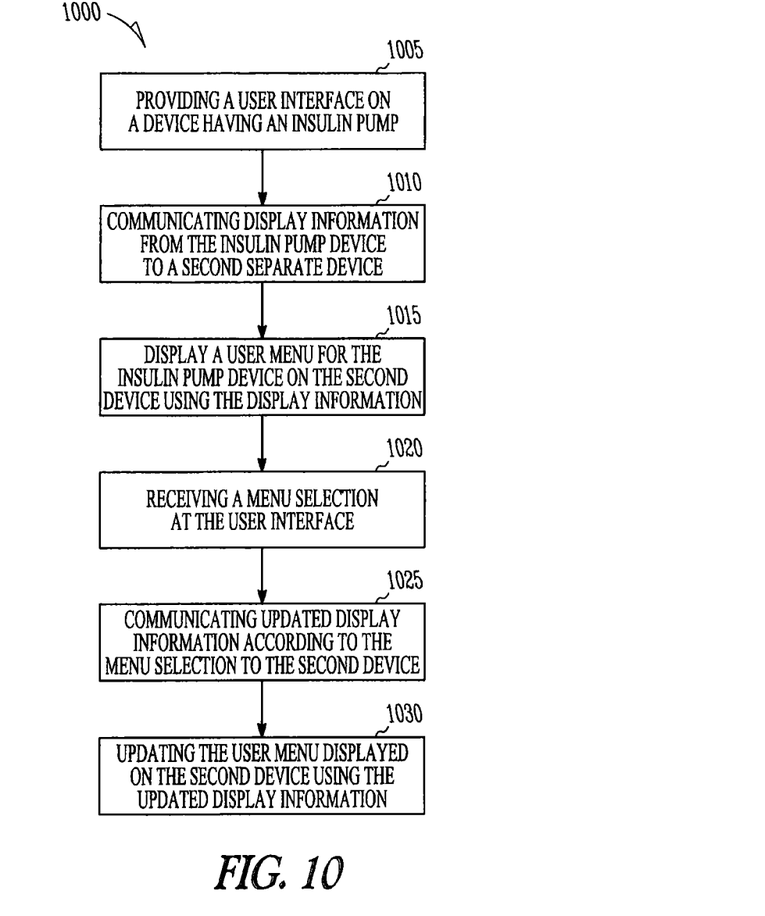
FIG. 10 is a flow diagram of another method of presenting a display for an insulin pump device.

FIG. 10 is a flow diagram of a method 1000 of presenting a display for an insulin pump device. At block 1005, a user interface is provided on a device having an insulin pump. At block 1010, display information is communicated from the insulin pump device to a second separate device. At block 1015, displaying a user menu for the insulin pump device is displayed on the second device using the display information. In some embodiments, the display information is converted to a video format at the second device and displayed on a video monitor. At block 1020, a menu selection is received at the user interface of the insulin pump. The menu selection is a menu item displayed on second device. The menu selection may be to change an operating parameter, initiate insulin therapy, display a device status, or run a device diagnostic for example. At block 1025, updated display information is communicated to the second device according to the menu selection. At block 1030, the user menu displayed on the second device is updated using the updated display information.

Figure 11:
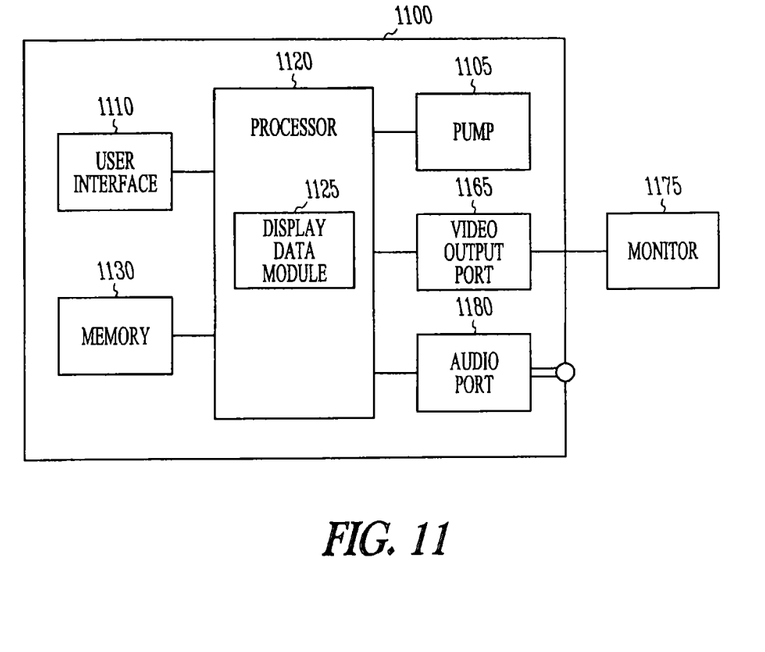
FIG. 11 is a block diagram of portions of an embodiment of an insulin pump device having an alternative display.

FIG. 11 is a block diagram of portions of an embodiment of an insulin pump device 1100 having an alternative display. The insulin pump device 1100 includes a pump 1105 configured to deliver insulin, a video output port 1165, and a processor 1120 communicatively coupled to the pump 1105 and the video output port 1165. The processor 1120 includes a display data module 1125 that communicates video display information via the video output port to a second separate device, such as a video monitor 1175 for example. The insulin pump device 100 is connected to the monitor 1175 via the video output port 1165.

In some embodiments, the video output port 1165 is an analog video output. The display data module 1125 provides the video display information in an analog video format at the video output port 1165. Examples of analog video formats provide by the display data module 1125 include, among other things, composite video, S video, component video, and VGA. In some embodiments, the video output port 1165 is a digital video output. The display data module 1125 provides the video display information in a digital format at the video output port 1165. Examples of digital video formats provide by the display data module 1125 include, among other things, High Definition Multimedia Interface (HDMI) and Digital Visual Interface (DVI).

In some embodiments, the insulin pump device 1100 includes a user interface 1110. The display data module 1125 converts input received via the user interface 1110 into changes to a display and communicates updated video display information according to the received input via the video output port. In this way, the monitor 1175 acts as a display for the insulin pump device 1100. The user interface 1110 may include a display screen on the insulin pump device 1100. The display data module 1125 may provide updated data to both the user interface display and the monitor 1175. The monitor 1175 may thereby function as an enlarged version of the device display screen.

In some embodiments, the insulin pump device 1100 includes a memory 1130. The memory 1130 stores one or more files containing video data. The display data module 1125 plays a video data file via the video output port 1165. The video data file may include training material, and the video data file provides a video tutorial to the user on the monitor 1175 when played. In some embodiments, the insulin pump device 1100 plays the video data file in response to an input received at the user interface 1110, such as an indication of menu selection for example.

In some embodiments, the insulin pump device 1100 includes an audio port 1180. The memory 1130 may store one or more files containing audio data. The display data module 1125 is configured to play the audio data file via the audio port 1180 in association with playing the video data file. In some embodiments, if the format of the file allows audio and video to be combined, the audio and video files may be provided by a single output port. The audio file may indicate a pump-related alarm or alert, or the audio file may accompany the training video.

Figure 12:
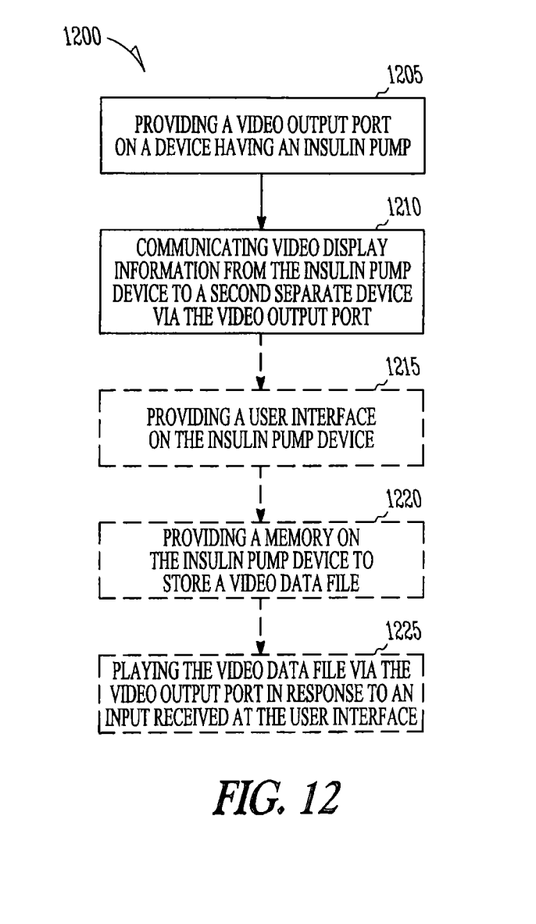
FIG. 12 is a flow diagram of another method of presenting a display for an insulin pump device.

FIG. 12 is a flow diagram of another method 1200 of presenting a display for an insulin pump device. At block 1205, a video output port is provided on a device having an insulin pump. At block 1210, video display information is communicated from the insulin pump device to a second separate device via the video output port. The second device may be a monitor or a television depending on the video format. Thus, the pump is a video driver for the second device.

As further shown in FIG. 12, in some embodiments the method 1200 includes, at block 1215, providing a user interface on the insulin pump device. At block 1220, providing a memory is provided on the insulin pump device to store one or more video data files. At block 1225, the video data file is played via the video output port in response to an input received at the user interface.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 CFR § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An ambulatory pump system, comprising:
   a user interface including a color display configured to display information to a user in a plurality of colors;
   a memory configured to store parameters relating to operation of an ambulatory infusion pump; and
   a processor configured to control the information displayed on the color display, the processor further configured to:
      display information relating to the status of the ambulatory infusion pump on a portion of the color display;
      detect a change in status of the medical infusion pump; and
      change the portion of the color display from one color to another color in response to the change in the status of the ambulatory infusion pump.

2. The ambulatory pump system as claimed of claim 1, wherein the change in the status of the pump relates to a device battery having a capacity less than a threshold battery capacity value.

3. The ambulatory pump system of claim 1, wherein a change in the color of the portion of the display screen includes a change in a text color.

4. The ambulatory pump system of claim 1, wherein the user interface is part of the pump.

5. The ambulatory infusion pump system of claim 1, wherein a change in the color of the portion of the color display includes altering a color of a portion of a background of the color display.

6. The ambulatory infusion pump system of claim 1, wherein a change in the color of the portion of the color display includes displaying a color flashing indicator.

7. The ambulatory infusion pump system of claim 1, wherein the change in status of the ambulatory infusion pump relates to a level of insulin in the ambulatory infusion pump.

8. An ambulatory infusion pump system, comprising:
   a user interface including a color display configured to display information to a user in a plurality of colors;
   a memory configured to store parameters relating to treatment of the user with an ambulatory infusion pump, including one or more thresholds related to glucose levels of the user; and
   a processor configured to control the information displayed on the color display, the processor further configured to:
      receive information relating to glucose levels of the user;
      display information relating to a recent glucose level of the user on a portion of the display in a first color;
      compare the information relating to glucose levels of the user to the one or more thresholds related to glucose levels of the user; and
      change the information relating to a recent glucose level of the user on the portion of the color display from the first color to a second color at the time when a glucose level of the user passes one of the one or more thresholds related to glucose levels of the user.

9. The ambulatory infusion pump system of claim 8, further comprising an ambulatory infusion pump.

10. The ambulatory infusion pump system of claim 9, wherein the user interface is part of the ambulatory infusion pump.

11. The ambulatory infusion pump system of claim 9, wherein the user interface is part of a device that is separate from the ambulatory infusion pump.

12. The ambulatory infusion pump system of claim 8, wherein comparing the information relating to glucose levels of the user to the one or more thresholds related to glucose levels of the user includes comparing glucose levels of the user to a high glucose threshold and to a low glucose threshold.

13. The ambulatory infusion pump system of claim 12, wherein the processor is configured to alter the color of the portion of the color display when the glucose level of the user is higher than the high glucose threshold.

14. The ambulatory infusion pump system of claim 12, wherein the processor is configured to alter the color of the portion of the color display when the glucose level of the user is lower than the low glucose threshold.

15. The ambulatory infusion pump system of claim 8, wherein altering the color of the portion of the color display includes altering a color of text on the color display.

16. The ambulatory infusion pump system of claim 8, wherein altering the color of the portion of the color display includes altering a color of a portion of a background of the color display.

17. The ambulatory infusion pump system of claim 8, wherein altering the color of the portion of the color.

* * * * *